(12) United States Patent
Chen et al.

(10) Patent No.: US 10,863,923 B2
(45) Date of Patent: Dec. 15, 2020

(54) SPIROMETER, MOUTHPIECE TUBE AND INSPECTION METHOD THEREOF

(71) Applicant: Chia-Hung Chen, New Taipei (TW)

(72) Inventors: Chia-Hung Chen, New Taipei (TW);
Hsiao-Pao Yen, New Taipei (TW);
Chia-Chi Su, Taichung (TW);
Liang-Lin Yen, Taipei (TW)

(73) Assignee: Chia-Hung Chen, New Taipei (TW)

( * ) Notice: Subject to any disclaimer, the term of this patent is extended or adjusted under 35 U.S.C. 154(b) by 180 days.

(21) Appl. No.: 15/677,168

(22) Filed: Aug. 15, 2017

(65) Prior Publication Data

US 2018/0055413 A1 Mar. 1, 2018

Related U.S. Application Data

(60) Provisional application No. 62/374,926, filed on Aug. 15, 2016.

(51) Int. Cl.
*A61B 5/08* (2006.01)
*A61B 5/087* (2006.01)
(Continued)

(52) U.S. Cl.
CPC .............. *A61B 5/087* (2013.01); *A61B 5/097* (2013.01); *A61B 8/4427* (2013.01);
(Continued)

(58) Field of Classification Search
CPC ....... A61B 5/087; A61B 5/0871; A61B 5/097; A61B 8/5223; A61B 8/4444; A61B 8/4427
See application file for complete search history.

(56) References Cited

U.S. PATENT DOCUMENTS 3,157,153 A * 11/1964 Moe ...................... A01M 29/18
116/137 R
2014/0106324 A1* 4/2014 Adams ................ A61M 15/009
434/262
(Continued)

FOREIGN PATENT DOCUMENTS

JP     H05505969      9/1993
JP     2014064675     4/2014
(Continued)

OTHER PUBLICATIONS

Taiwan Patent Office "Office Action" dated May 30, 2018, Taiwan.
(Continued)

*Primary Examiner* — Navin Natnithithadha
*Assistant Examiner* — Andrey Shostak
(74) *Attorney, Agent, or Firm* — WPAT, PC

(57) ABSTRACT

Spirometer, mouthpiece tube and inspection method thereof. The spirometer includes at least the mouthpiece tube and an ultrasound detector configured to detect the ultrasound generated by the gas flowing through the mouthpiece tube, wherein the mouthpiece tube has a shell having an opened end, a closed or opened end, and an ultrasonic generator configured to be inserted into different portions of the shell in different situations. Therefore, by inserting the ultrasonic generator into different portions of the shell during expiration and inspiration, the gas flow during expiration and inspiration may be converted into the ultrasonic signal and then maybe detected and analyzed.

7 Claims, 9 Drawing Sheets

(51) Int. Cl.
*A61B 5/097* (2006.01)
*A61B 8/00* (2006.01)
*A61B 8/08* (2006.01)

(52) U.S. Cl.
CPC .......... *A61B 8/4444* (2013.01); *A61B 8/5223* (2013.01); *A61B 5/0871* (2013.01)

(56) References Cited

U.S. PATENT DOCUMENTS

2014/0166004 A1* 6/2014 Pierro .................. A61M 16/14
128/203.12
2017/0319106 A1* 11/2017 Nassehi ............... A61B 5/6898

FOREIGN PATENT DOCUMENTS

| | | |
|---|---|---|
| JP | 2014117429 | 6/2014 |
| JP | 2016157707 | 9/2016 |
| JP | 2017035485 | 2/2017 |
| MX | 2012014916 | 6/2014 |

OTHER PUBLICATIONS

Japan Patent Office "Office Action" dated Nov. 13, 2018, Japan.
Japan Patent Office "Office Action" dated Jul. 30, 2019, Japan.
EzOxygen Genius "https://www.youtube.com/watch?v=i9uGqJ7DFMg", Jul. 31, 2017, Youtube.

* cited by examiner

SPIROMETER, MOUTHPIECE TUBE AND INSPECTION METHOD THEREOF

FIELD OF THE INVENTION

The present invention is related to a spirometer, a mouthpiece tube and an inspection method thereof, especially, the present invention is related to the spirometer, the mouthpiece tube and the inspection method that converts the gas flow during inspiration and expiration into the ultrasonic signal for detecting and analyzing.

BACKGROUND OF THE INVENTION

Currently, the plastic impedance pressure spirometer and the turbine spirometer are the most popular spirometers on the market. The former utilizes the wind pressure in the gas flowing through the spirometer during breath to induce the sheets oscillation of the sheet sensor positioned on the end or the side of the spirometer for generating the corresponding inspiration and/or expiration signal, and the latter utilizes the wind pressure in the gas flowing through the spirometer during breath to drive the fan leaves and/or turbines and then measure the generated current or measure the rotation of the fan leaves and/or turbines by the infrared ray for generating the corresponding inspiration/expiration signals. However, these currently available spirometers still have some disadvantages to be improved. For example, due to the inertia, the motion of the sheets, the fan leaves and the turbines can not be stopped immediately when the gas flow is terminated so that the inspiration/expiration signal is continuously generated for a when after the end of the gas flow. For example, due to the weight and the friction, the sheets, the fan leaves and the turbines usually can not precisely generate the inspiration/expiration signal if the gas flow volume or the gas flow rate is lower. For example, due to the manufacturing errors and the operational loss, both the deviation and degradation of the measurement qualify are usually unavoidable and also the measurement result is hard to correct. Accordingly, there is a need to develop a new spirometer.

SUMMARY OF THE INVENTION

The present invention utilizes the ultrasonic wave to generate the inspiration and/or expiration signal, i.e., both the ultrasonic wave generation device and the ultrasonic wave detection device are used to replace the sheets, the fan leaves or the turbines utilized by the well-known spirometers. By delivering the gas generated during expiration and/or expiration through the ultrasonic wave generation device (such as silent whistle and Galton's whistle) positioned on the mouthpiece tube, the corresponding ultrasonic signals may be generated. After that, by analyzing the ultrasonic signals, some messages of the inspiration and/or expiration may be acquired, such as the gas flow volume and the gas flow rate.

The invention proposes the mouthpiece tube having a shell and an ultrasonic wave generation device. The shell has an open end and at least one opening positioned on the sidewall of the shell, and the ultrasonic wave generation device may be positioned on different portions of the shell. For example, the ultrasonic wave generation device may be positioned on the open end of the shell so that the gas may flow from the gas entrance of the ultrasonic wave generation device though the gas exit of the ultrasonic wave generation device and then leave through the opening on the shell. For example, the ultrasonic wave generation device may be positioned on the opening on the sidewall of the shell where the gas entrance and the gas exit of the ultrasonic wave generation device is positioned outside and inside the space enclosed by the shell respectively, hence the gas may flow through the gas entrance and the gas exit in sequence and then leave through the open end of the shell. Accordingly, the gas flow generated during the inspiration and/or the expiration may generate the corresponding ultrasonic wave signal respectively.

The invention proposes the spirometer having the mouthpiece tube configured to convert the gas flow of the breath gas (i.e., the gas appeared during the expiration and/or the inspiration) into the ultrasonic wave signals and the ultrasonic wave detection device (such as the microphone) configured to receive the ultrasonic wave signal from the mouthpiece tube. Besides, the spirometer may further has a process device configured to convert the ultrasonic wave signal into the signal data related to the gas flow (such as the gas flow rate time diagram or the gas flow volume time diagram), and also may further a communication device (such as wireless network device or bluetooth device) configured to transmit the ultrasonic wave signal to the device (such as cell phone and computer) positioned outside the spirometer for analyzing the ultrasonic wave signal. Moreover, the spirometer may further have a shell where the mouthpiece tube may be connected to the shell via the joint ring or other device. Also, each of the ultrasonic wave detection device, the process device and the communication device may be positioned inside the space enclosed by the shell or be integrated with the mouthpiece tube.

The invention proposes the inspection method using the spirometer and the mouthpiece tube mentioned above. Initially, use the spirometer configured to convert the gas flow during inspiration and/or expiration into the ultrasonic wave signal so as to convert the gas flow during inspiration/expiration into the ultrasonic wave signal during the breath function inspection. After that, analyze the ultrasonic wave signal so as to acquire the gas flow rate time diagram or other data related to the inspiration and/or the expiration and then generate the corresponding breath function parameters values.

The invention has some advantages in comparison to the currently popular plastic impedance pressure spirometer and turbine spirometer. First, it is low cost and easy to make, because both the silent whistle and Galton's whistle are current commercial product and also the ultrasonic wave detection device is the well-known skill. Next, because the ultrasonic wave generation device may generate the ultrasonic wave immediately if the gas is flowing (or the gas flow is larger than the threshold value) and may stop the generation of the ultrasonic wave immediately if the gas flow is finished (or the gas flow is smaller than the threshold value), it is more sensitive than the conventional spirometers whose motion inertia induces the generation of the expiration/inspiration signals for a while after the finish of the gas flow. Moreover, because the ultrasonic wave generation device (such as silent whistle, Galton's whistle, or other equivalents) generates the ultrasonic wave by using the gas vibrations of the gas flowing through a briefly close space, the operating loss is less and the measured distortion induced by the smaller vibrations (or viewed as weaker gas flow) may be decreased, especially if the generated ultrasonic wave signal may be adjusted by adjusting the size and the shape of the briefly close space. In addition, all of the silent whistle, the Galton's whistle, the microphone and the circuits formed by the modern technology may have higher

DETAILED DESCRIPTION OF THE INVENTION

Preferred embodiments of the present invention will be described in reference to the accompanying drawings.

The invention deliveries the inspiration and/or expiration gas through the ultrasonic wave generation device so as to generate the ultrasonic wave signal related to the gas flow during inspiration and/or expiration. Hence, the breath status may be mastered by analyzing the ultrasonic wave signal, such as by continuously converting the measured ultrasonic wave signal into the gas flow rate time diagram. In other words, the invention uses both the ultrasonic wave generation device and the ultrasonic wave detection device to replace the device used to measure the gas flow by the well-known spirometers (such as the plastic impedance pressure spirometer and the turbine spirometer). Further, both the ultrasonic wave generation device and the ultrasonic wave detection device may be formed by the currently available technologies. For example, the well-known silent whistle and Galton's whistle may be used to convert the flow of the gas delivered through into the ultrasonic wave signal, wherein the strength of the generated ultrasonic wave is dependent on the flow rate of the gas delivered through. For example, the ultrasonic detection device may be formed by using many well-known technologies, such as omnidirectional microphone, bidirectional microphone, cardioid microphone, super novel directional microphone, gun shape directional microphone and so on.

The invention may acquire more sensitive gas flow rate time diagrams than the conventional spirometers, and then the invention may more precisely and stably measure the breath status. Note that the ultrasonic wave generation device only generates the ultrasonic wave of the situation that the gas is delivered through. Besides, on the base of the acquired gas flow rate time diagram, the well-known technologies may be used to find the breath parameters values, such as the peak inspiratory flow rate, the first second inspiratory volume, the forced vital capacity or others.

Figure 1A:
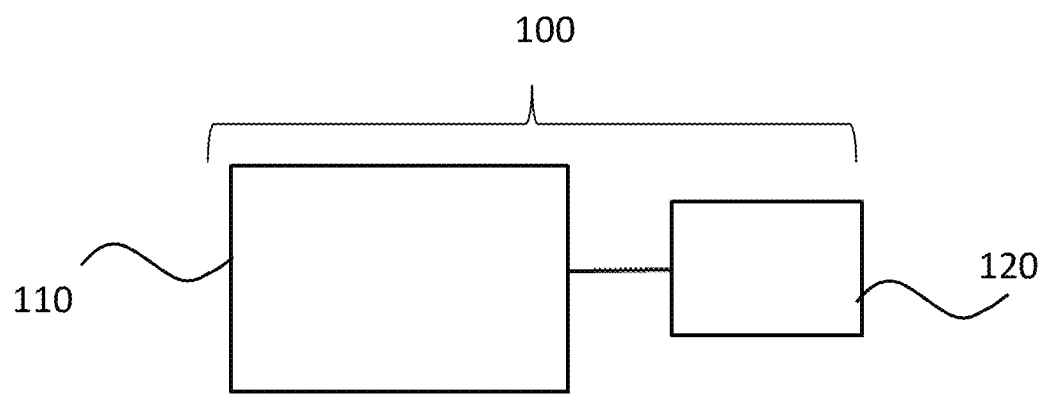
FIG. 1A to FIG. 1D are the illustrations of the spirometer according to some embodiments of the invention.
Figure 1B:
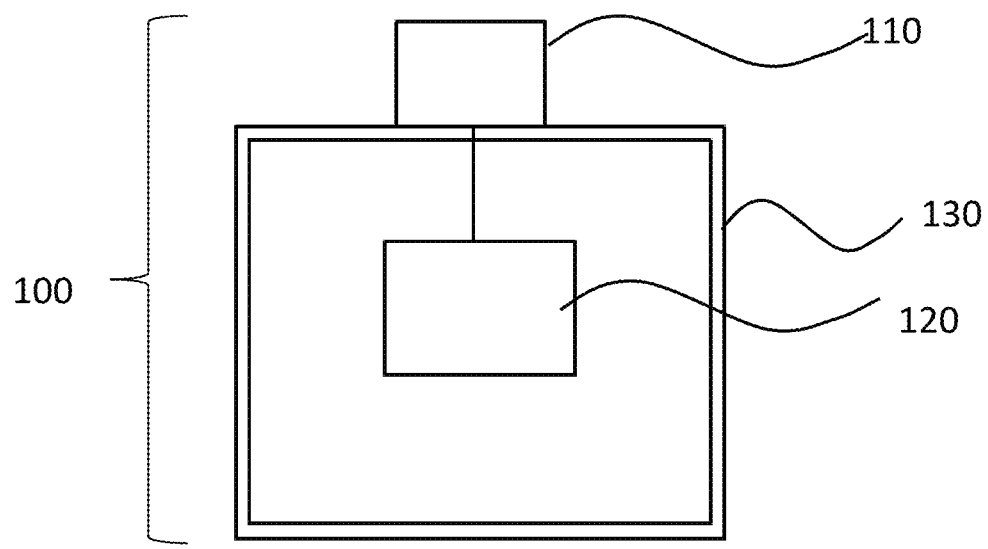

One embodiment of the invention is the spirometer, especially the spirometer uses the mouthpiece tube capable of converting the gas flow into the ultrasonic wave signal. As shown in FIG. 1A, the spirometer 100 has the mouthpiece tube 110 configured to convert the gas flow during inspiration and/or expiration into the ultrasonic wave signal and the ultrasonic wave detection device 120 (such as the microphone) configured to receive the ultrasonic wave signal propagated from the mouthpiece tube 110. On some embodiments, the ultrasonic wave detection device 120 may be integrated with the mouthpiece tube 110, i.e., the mouthpiece tube 110 may convert the gas flowing through into the ultrasonic wave signal and also may detect the ultrasonic wave signal in such situation. On some embodiments, as shown in FIG. 1B, the spirometer 100 has the shell 130, the mouthpiece tube 110 may be connected to the shell 130 via the joint ring or other elements positioned on the shell 130, and the ultrasonic wave detection device 120 may be positioned in the space enclosed by the shell 130. Moreover, the mouthpiece tube 110 may be removed away the shell 130 and also may be fixed on the shell 130. In this way, the mouthpiece tube 110 may be a replaceable element so that different users may their own mouthpiece tubes respectively.

Figure 1C:
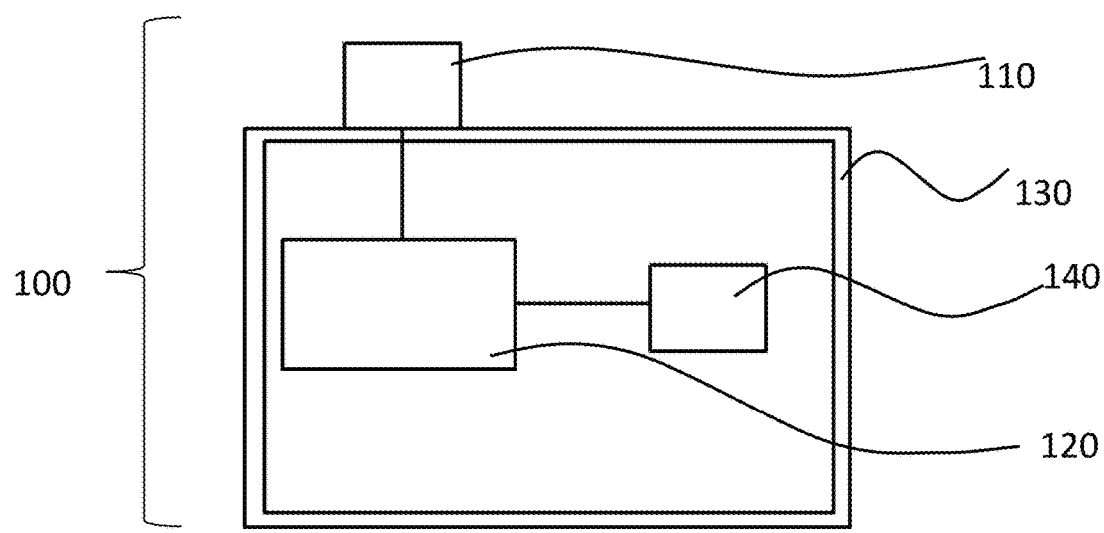
Figure 1D:
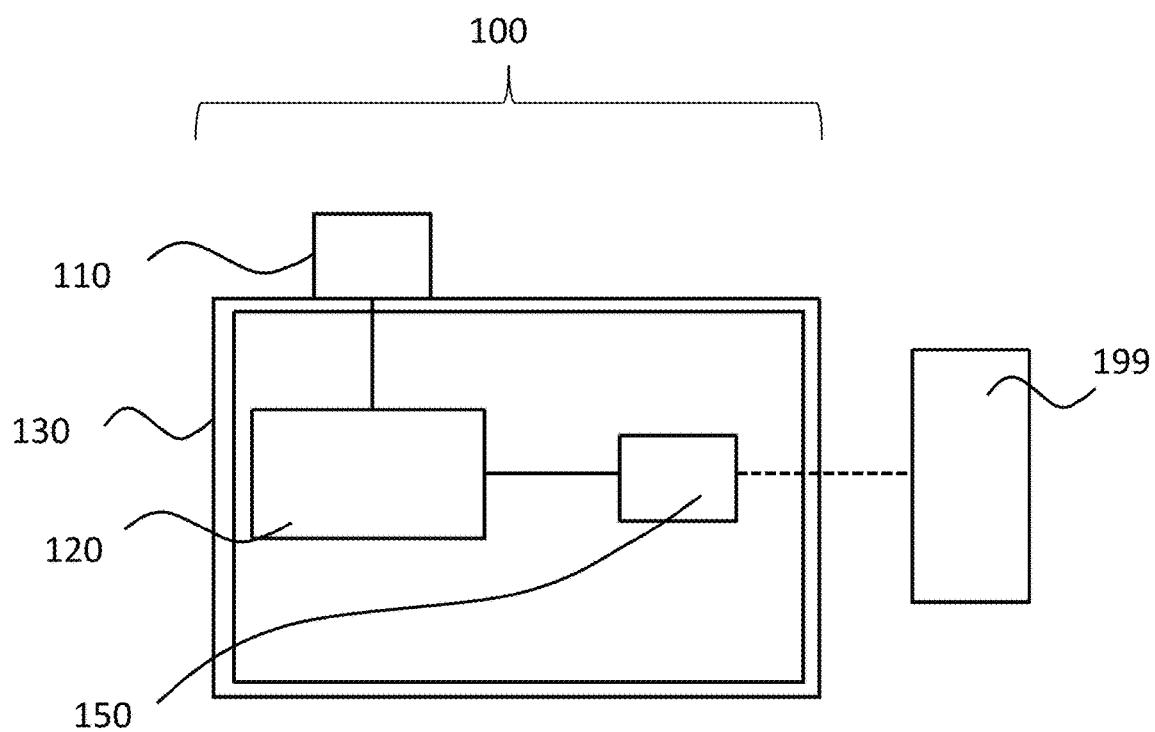

On some embodiments, the spirometer 100 has the process device 140 configured to convert the ultrasonic wave signal into the message data related to the gas flow, wherein the process device 140 also is positioned in the space enclosed by the shell 130 as shown in FIG. 1C. On some embodiments, as shown in FIG. 1D, the spirometer 100 has the communication device 150 (such as the wireless network element or the bluetooth element) configured to transmit the ultrasonic wave signal into the external device 199 (such as cell phone or computer) for analyzing the ultrasonic signal. In other words, the spirometer 100 may be a product capable of performing the processes of receiving the breath gas to analyzing the ultrasonic wave signal, but also may be a product only receive the breath gas and generate the corresponding ultrasonic wave signal where the analysis of the ultrasonic wave signal is processed by cell phone, computer or others.

The geometric details of the mouthpiece tube 110, such as size and shape, especially the shape, the size or others of the connection interface between the mouthpiece tube 110 and the spirometer 100 is flexible. It may be equal to the size and the shape of the mouthpiece tube used by the well-known spirometer, but also may have different designs according to the practical requirements. In some other embodiments, each of the ultrasonic wave detection device 120, the process device 140 and the communication device 150 may be positioned in the space enclosed by the shell 130 but also may be integrated into the mouthpiece tube 110, i.e., the shell 130 may be omitted. The invention does not limit these variations also does not present all variations in drawings.

Figure 2A:
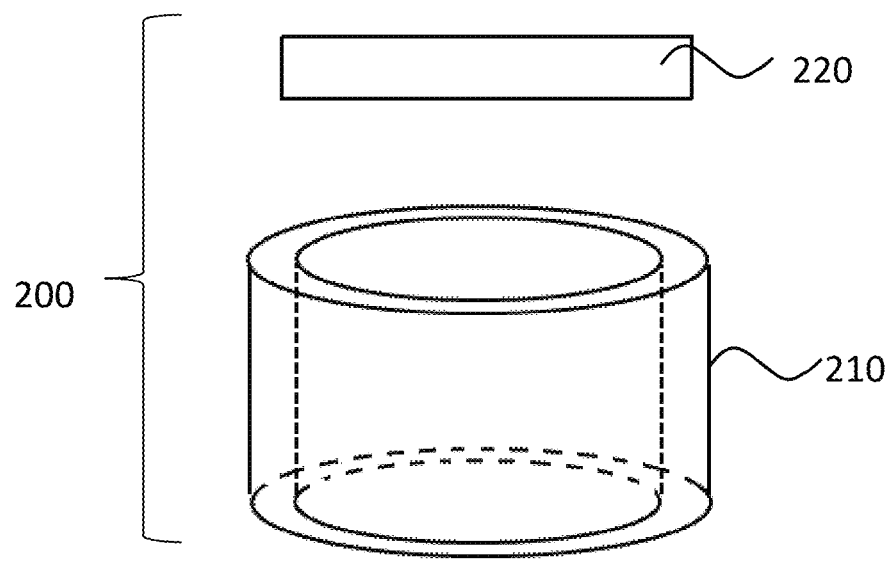
FIG. 2A to FIG. 2D are the illustrations of the mouthpiece tube according some embodiments of the invention.

Another embodiment of the invention is the mouthpiece tube, especially the mouthpiece tube capable of converting the gas flow into the ultrasonic wave signal. As shown in FIG. 2A, the essential structure of the present mouthpiece tube 200 has the shell 210 and the ultrasonic wave generation device 220. The ultrasonic wave signal corresponding to the gas flow status (such as gas flow rate) is generated whenever the inspiration and/or expiration gas flows through the ultrasonic wave generation device 220. For example, whenever the user exhales and/or inhales as the user's mouth touches or approaches the mouthpiece tube 200. In the situation that the ultrasonic wave detection device 120 is positioned in the space enclosed by the shell 130 of the spirometer 100 and the shell 210 of the mouthpiece tube 200 is connected to the shell 130 via junction ring or others, the shell 210 also may fix the distance between the ultrasonic wave generation device 220 and the ultrasonic wave detection device 120. On some other embodiments, the shell 210 and the mouthpiece tube used by the well-known spirometer may have the same size, the same shape and others, especially the size and the shape of the interface between the shell 210 and the shell 130. Nevertheless, it also may be different than the size and the shape of the mouthpiece tube used by the conventional spirometer.

Figure 2B:
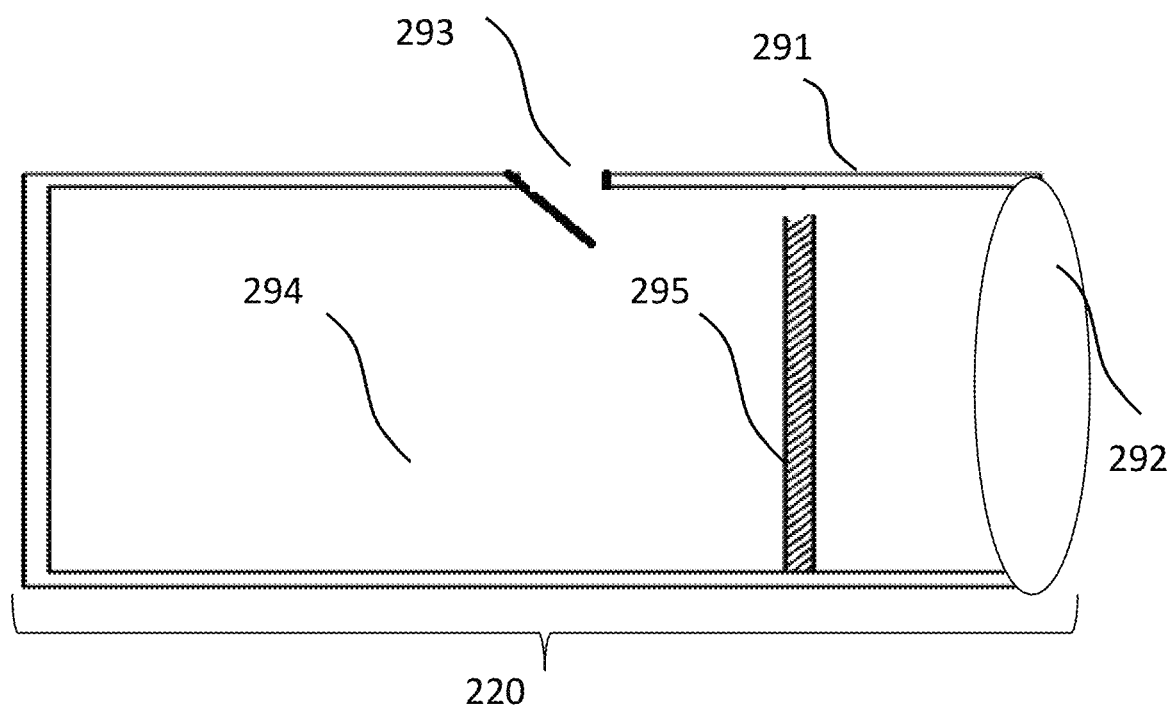

In some embodiments, the ultrasonic wave generation device 220 is the conventional silent whistle such as the conventional Galton's whistle. The advantages of such approach are low cost and simple technology because the development of new device is not required. As shown in FIG. 2B, the essential structure of the well-known silent whistle and the well-known Galton' whistle has an open end 292 and an opposite end which may be open or close. It has an inner space 294 located between the two ends, a cut 293 is positioned on the sidewall of its' whistle shell 291 and faces the inner space 294, and a spoiler 295 is positioned inside the inner space 294 and placed between the open end 292 and the cut 293. During the gas flow path from the open end 292 through the inner space 294 to the cut 293, the ultrasonic wave is generated by the gas disturbance induced by the interaction between the gas and the spoiler 295. Further, the strength of the generated ultrasonic wave is essentially dependent on the gas flow rate and the frequency of the generated ultrasonic wave is essentially dependent on the shape and the size of the inner space 294.

Figure 2C:
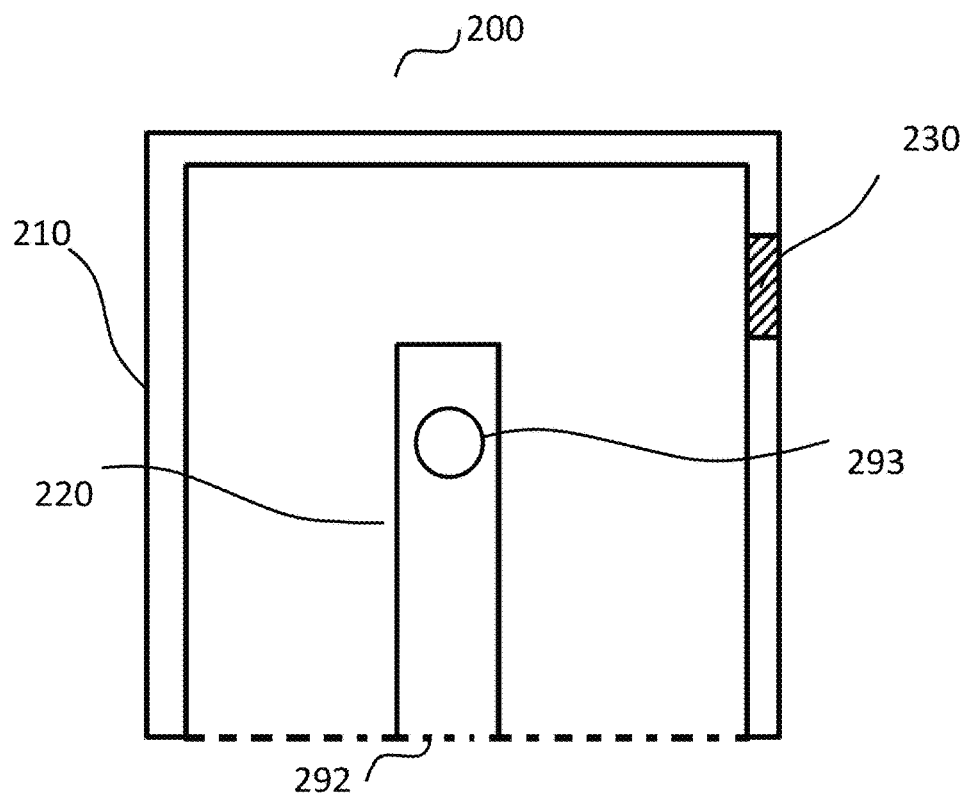
Figure 2D:
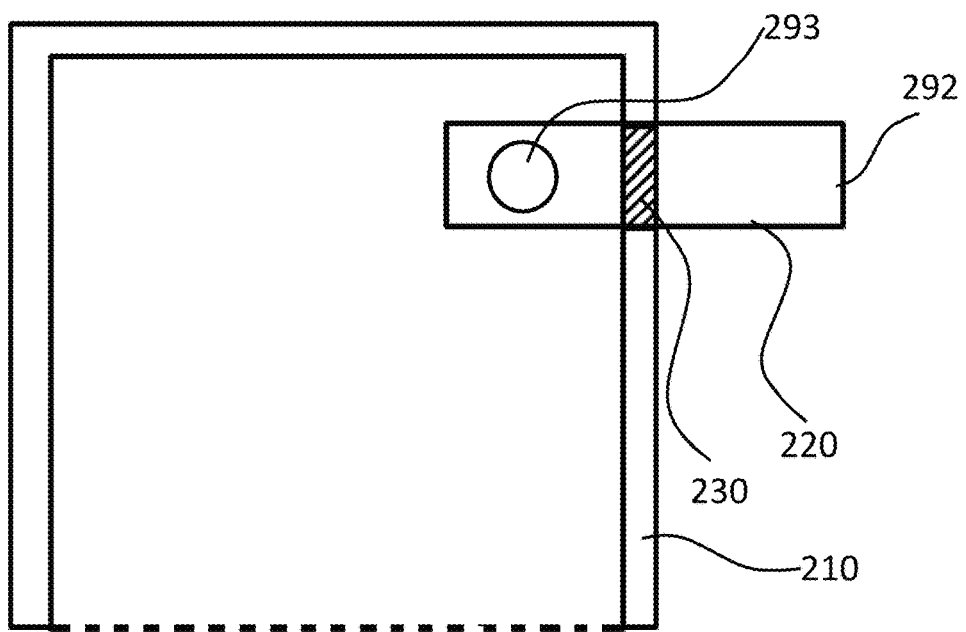

In the situation that the ultrasonic wave generation device 220 is the well-known silent whistle or the well-known Galton's whistle, one end of the shell 210 is closed (the gas can not flow through) and another end of the shell 210 is opened (the gas can flow through), one cut 293 is positioned on the sidewall of the shell 210, and the ultrasonic wave generation device 220 is positioned on different portions of the shell 210 for monitoring the inspiration status or the expiration status respectively. For example, as shown in FIG. 2C, in the situation that the expiration status is measured, the ultrasonic wave generation device 220 is positioned on the open end 292 of the ultrasonic wave generation device 220 so that the gas may flow from the open end 292 through the spoiler 295 and the cut 293 in the inner space 294 of the ultrasonic wave generation device 220 in sequence and then may leave through the cut 293 of the shell 210. For example, as shown in FIG. 2D, in the situation that the inspiration status is measured, the ultrasonic wave generation device 220 is positioned in the gas opening 230 of the sidewall of the shell 210 where the open end 292 and the cut 293 of the ultrasonic wave generation device 220 is positioned outside and inside the space enclosed by the shell 210 respectively. In this way, the gas may from the open end 292 through the spoiler 295 inside the inner space 294 of the ultrasonic wave generation device 220 and the cut 293 in sequence, and then leaves through the open end of the shell 210. Therefore, the different gas flows of the expiration and the inspiration may be converted into different ultrasonic wave signals by the ultrasonic wave generation device.

Figure 3:
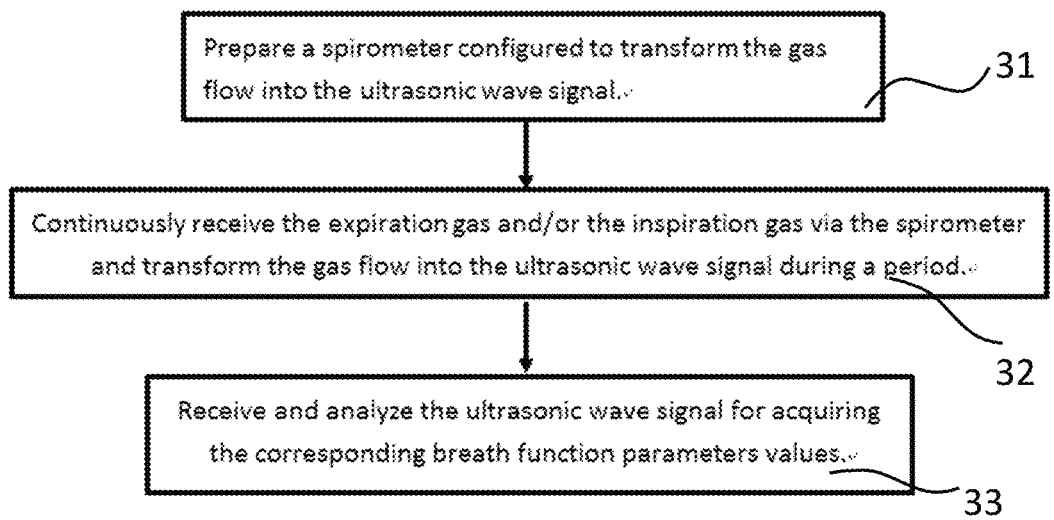
FIG. 3 is the essential flow chart of the inspection method according to some embodiments of the invention.

Some embodiments are the breath function inspection method. These embodiments are applicable to these spirometers and these mouthpiece tubes mentioned above and their essential flow chart is shown in FIG. 3. Initially, as shown in the step block 31, prepare a spirometer configured to convert the gas flow into the ultrasonic wave signal. Next, as shown in the step block 32, continuously receive the expiration gas and/or the inspiration gas via the spirometer and convert the gas flow into the ultrasonic wave signal during a period. Then, as shown in step block 33, receive and analyze the ultrasonic wave signal for acquiring the corresponding breath function parameters values.

Figure 4A:
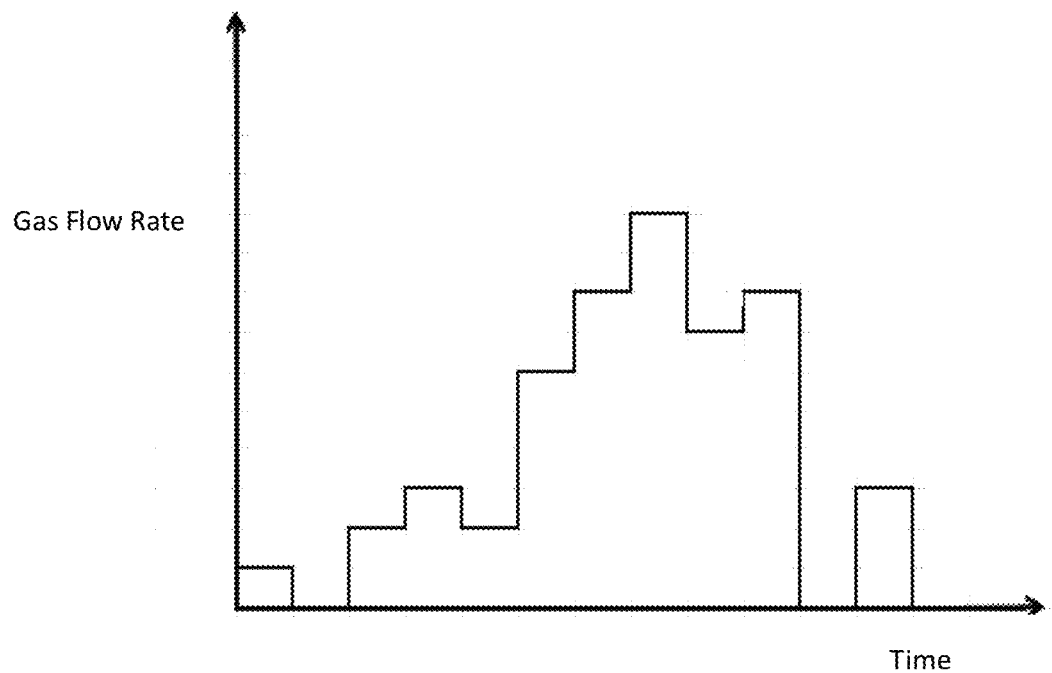
FIG. 4A and FIG. 4B are the illustrations of the gas flow messages according to some embodiments of the invention.
Figure 4B:
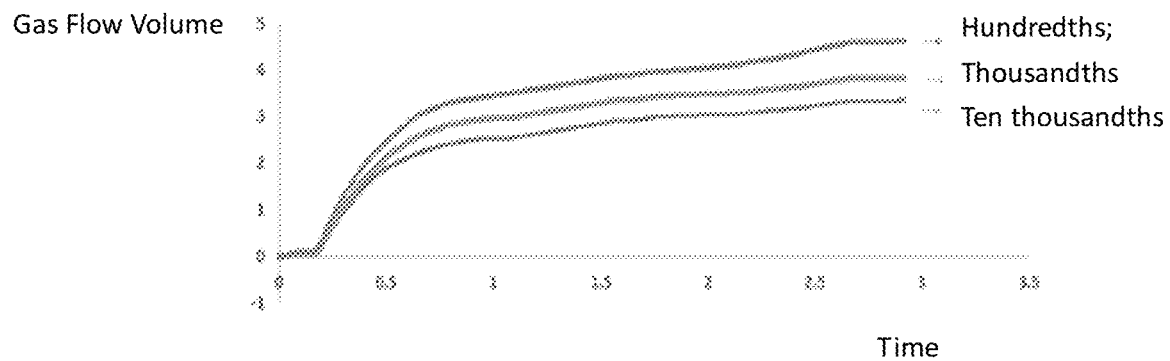

For example, the continuously generated ultrasonic wave signal during this period may be converted into the gas flow rate time diagram, such as the qualitative example shown in FIG. 4A, related to the inspiration function and/or the expiration function. Hence, the inspiration related breath functions may be decided by the maximum flow rate or whether the flow rate excess the threshold during the inspiration period, and also may be decided by the flow volume diagram based on the relationship between the flow rate and time (e.g. the integration of the flow rate time diagram) as shown in FIG. 4B during the inspiration period. Further, the peak value of the gas flow rate and/or the period that the gas flow rate exceeds the threshold may be used to measure the expiration function, but the accumulated gas flow volume of a period and/or the accumulated gas flow volume of a period that the gas flow rate is higher than the threshold may be used to measure the inspiration function.

It should be emphasized that all of the ultrasonic wave generation device (such as silent whistle and Galton's whistle), the ultrasonic wave detection device (such as these microphones mentioned above) and the process device (may be practiced by the integrated circuits or the applications software) may have higher qualify stability and lower loss. In contrast, all of the sheets, fan leaves and turbines used by the conventional spirometers are easy to be worn, hard to maintain manufacture qualify and trend to continuously generate the ultrasonic wave signal after the finish of the gas flow due to the motion inertia. Therefore, no matter to inspect the inspiration or to inspect the expiration, both the gas flow rate time diagram and the gas flow volume time diagram acquired by the invention using the ultrasonic wave may have jagged outline, i.e., the measurement of the gas flow is sensitive to the variation in the gas flow. Especially, human' inspiration will be gradually slow down before the lung is full but human's expiration will be fluctuated with unstable gas flow rate before the lung is empty. Hence, the turbines, the fan leaves and the plastic sheets used by the conventional spirometer can not precisely measure due to the gas flow rate variation during the inspiration period. In contrast, the ultrasonic wave inspection used by the invention may generate the ultrasonic wave if the gas is flowing and may stop generating the ultrasonic wave if the gas flow is stopped. In this way, the benefits of the proposed invention are more significant.

The proposed spirometer and the proposed mouthpiece tube may be further integrated with the mobile phone. Beside the situation that the mobile phone is used as the process device of the spirometer, some other non-illustrated embodiments may directly integrate the mouthpiece tube (includes the ultrasonic wave generation device) and the ultrasonic wave detection device into the mobile phone, or integrate the mouthpiece tube (includes the ultrasonic wave generation device) and the ultrasonic wave detection device as an external device connected to the mobile phone via the universal serial bus (USB) or other interface (eq., is alike to the earphone connected to the mobile phone via the headphone plug). Of course, on these situations, the used algorithm, at least the values of the parameters used by the algorithm, may be adjusted according to the different sensitivities of different micro phones and the distance between the micro phone and the ultrasonic wave generation device.

In the situation that the ultrasonic wave generation device used by the invention is the silent whistle, the Galton's whistle or other hardware capable of adjusting the frequency of the generated ultrasonic wave, the proposed invention may fix the frequency of the ultrasonic wave generated by the silent whistle or the Galson's whistle, i.e., the position of the spoiler 295 is fixed, also the invention may allow the ultrasonic wave frequency being adjustable, i.e., the position of the spoiler 295 is adjustable. The advantages of fixing the ultrasonic wave frequency are that the measurement and the calculation of the gas flow rate and the gas flow volume are simpler and then the required adjustable parameters of the used algorithm are reduced.

Figure 5A:
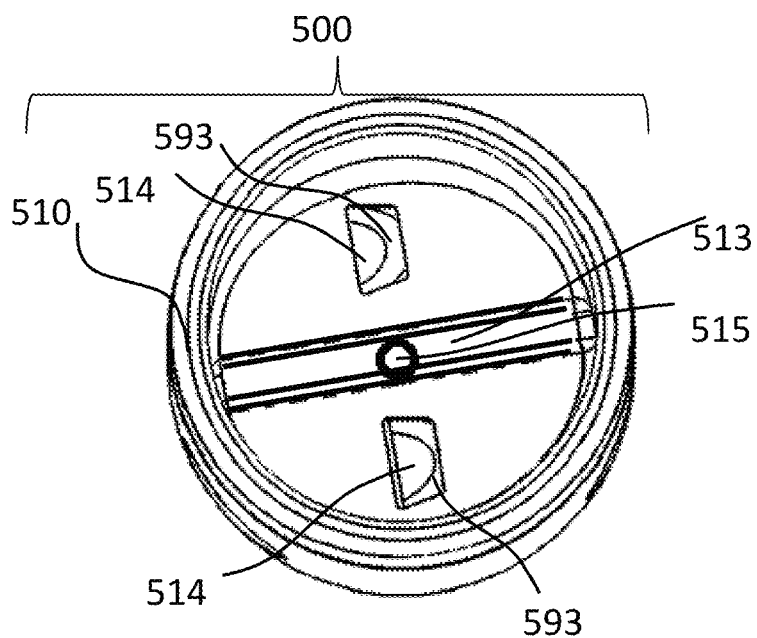
FIG. 5A to FIG. 5C are the illustrations of the structure of the mouthpiece tube according to one embodiment of the invention.
Figure 5B:
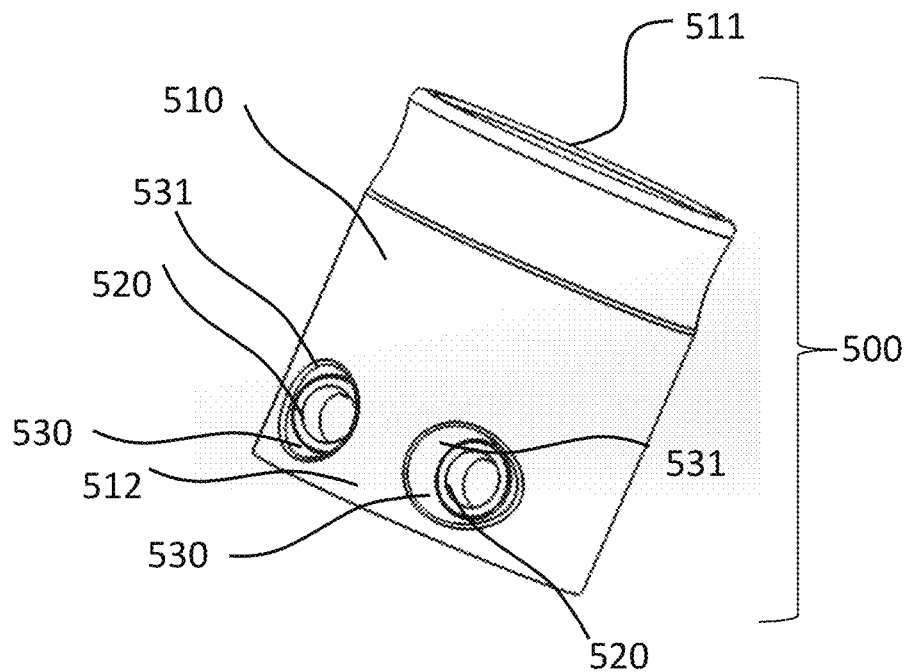
Figure 5C:
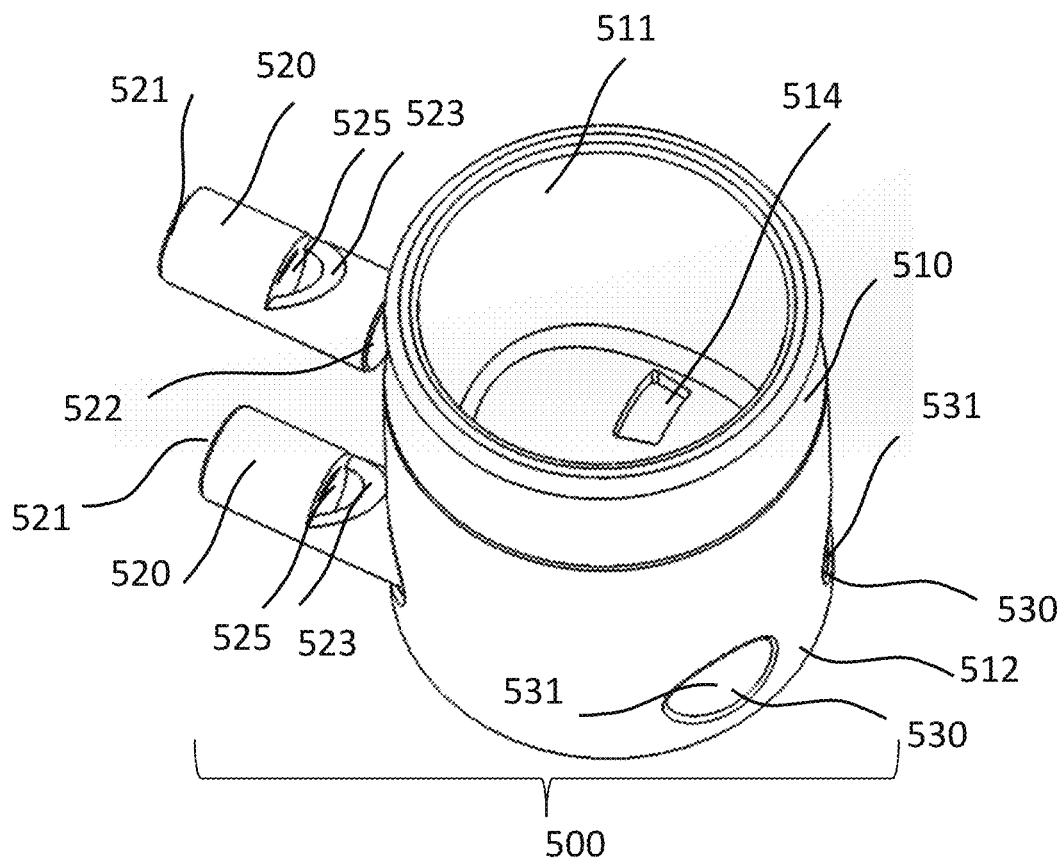

According to another embodiment of the invention, as shown in FIG. 5A to FIG. 5C, the invention provides a mouthpiece tube 500 configured to inspect the inspiration status. The mouthpiece tube 500 includes a shell 510 and at least one ultrasonic wave generation device 520. The shell 510 may be cylindrical, and two ends of the shell 510 are an exit end 511 and a shell bottom 512 respectively. Further, the shell bottom 512 may further to include a channel 530 for containing at least one ultrasonic wave generation device 520, wherein the channel 530 may be cylindrical. The channel 530 has a channel opening 531 for connecting to the exterior of the shell 510. The shell bottom 512 also has a gas opening 514 for connecting to the exit end 511 to form a gas flow space enclosed by the shell 510. The shell bottom 512 may further have at least one gas opening 515 and at least one groove 513 which is positioned between two neighboring channels and faces to the exit end 511, wherein the at least one groove 513 is located on the shell bottom 512 for separating different channels 530 and keeping each channel 530 being disconnected to and independent on other channel (s) 530, wherein the at least one gas opening 515 is connected to the exterior of the mouthpiece tube 500 for additionally introducing gas and then reducing the resistance of the gas flow. The gas opening 515 may be positioned on the groove 513 or other portions outside the channel 530. In addition, the ultrasonic wave generation device 520 may be tubular. The ultrasonic wave generation device 520 may further have a gas entrance 521, an ultrasonic wave generation device bottom 522, a gas exit 523 and a spoiler 525. The gas entrance 521 is positioned on one end of the ultrasonic wave generation device 520 for introducing the gas flow, the other end of the ultrasonic wave generation device 520 is the ultrasonic wave generation device bottom 522, and the gas exit 523 is positioned in the middle portion of the ultrasonic wave generation device 520. The spoiler 525 is positioned inside the ultrasonic wave generation device 520 and is placed between the gas entrance 521 and the gas exit 523. The spoiler 525 may be a baffle positioned in an inner space inside the ultrasonic wave generation device 520 for forming a narrow channel, wherein the inner space is distributed essentially between the gas entrance 521 and the gas exit 523 as shown in FIG. 5C. Hence, a gas disturbance is induced so that the gas flowing through the gas exit 523 has a special vibration. The ultrasonic wave generation device 520 is placed on the channel 530, and the gas exit 523 is connected to the gas opening 514 so that the gas is delivered from the inner space of the ultrasonic wave generation device 520 into the gas flow space enclosed the shell 510. Further, a first gas flow path from the gas entrance 521 into the ultrasonic wave generation device 520 is orthogonal to a second gas flow path from the gas exit 523 to the exterior of the ultrasonic wave generation device 520.

According to the embodiment, by referring to FIG. 5A to FIG. 5C, the application of the proposed mouthpiece tube 500 may be described as below. First, provides a gas flow suction for delivering the gas from the gas flow space enclosed by the shell 510 of the mouthpiece tube 500 to the exit end 511. When the gas flow suction begins to function, the gas outside the mouthpiece tube 500 is delivered through the gas entrance 521 to form a gas flow. Then, the gas flow is delivered through the spoiler 525 and the gas exit 523 to generate the ultrasonic wave (i.e., the gas flow may be viewed as the ultrasonic wave gas flow in such portion), and the gas flow is delivered through the gas opening 514 into the gas flow space enclosed by the shell 510. In the meantime, by using an ultrasonic wave detection device, the breath function may be distinguished by measuring and calculating the maximum flow rate of the inspiration or deciding whether the gas flow rate exceeds the threshold value. Besides, the direction of the gas delivered away the exit end 511 is orthogonal to the direction of the gas delivered into the gas entrance 521 of at least one ultrasonic wave generation device 520. On the other hand, the usage of the gas opening 515 may significantly reduce the gas flow resistance when the gas flow suction begins to function, because the path of the ultrasonic wave gas flow has an orthogonal corner herein.

According to one more embodiment of the invention, as shown in FIG. 6A to FIG. 6D, the invention provides a mouthpiece tube 600 configured to inspect the expiration status. The mouthpiece tube 600 includes a shell 610 and at least one ultrasonic wave generation device 620. The shell 610 may be cylindrical, also one end of the shell 610 is an entrance end 611 capable of delivering the external gas into the space surrounded by the shell 610 and another end of the shell 610 is an exit end 612. One fixed member 630 is positioned in the middle of the exit end 612, and at least a gas opening 614 is positioned on the sidewall of the shell 610. The fixed member 630 further has a fixed channel 631 further having a fixed channel positioner 633 and the gas opening 614 connecting the fixed channel 631 and the exterior of the space enclosed by the shell 610. Each ultrasonic wave generation device 620 may be tubular and further include a gas entrance 621, an ultrasonic wave generation device bottom, a gas exit 623, a spoiler 625, and a positioning component 626. The gas entrance 621 for importing gas is positioned on one end of the ultrasonic wave generation device 620, and the other end of the ultrasonic wave generation device 620 is the ultrasonic wave generation device bottom. The gas exit 623 is positioned in the middle portion of the ultrasonic wave generation device 620. The spoiler 625 is positioned inside the ultrasonic wave generation device 620 and placed between the gas entrance 621 and gas exit 623. The spoiler 625 may be a baffle configured to form a narrow opening. The positioning component 626 is matched with the fixed channel positioner 633 so that the ultrasonic wave generation device 620 may be simply and correctly constructed and positioned in the fixed channel 631 and also so that the gas exit 623 precisely connected with the gas opening 614 for delivering the gas away the gas flow space enclosed by the shell 610 through the inner of the ultrasonic wave generation device 620. Further, a first gas flow path from the gas entrance 621 into the ultrasonic wave generation device 620 is orthogonal to a second gas flow path from the gas exit 623 to the exterior of the ultrasonic wave generation device 620.

Figure 6A:
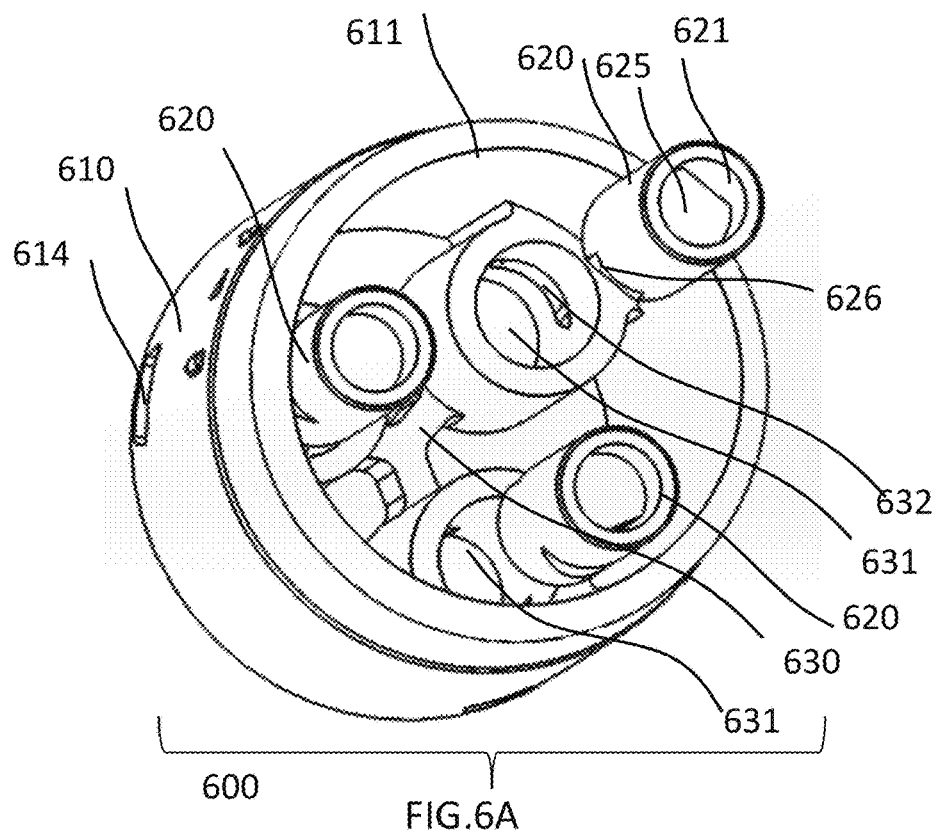
FIG. 6A to FIG. 6D are the illustrations of the structure of the mouthpiece tube according to one embodiment of the invention.
Figure 6B:
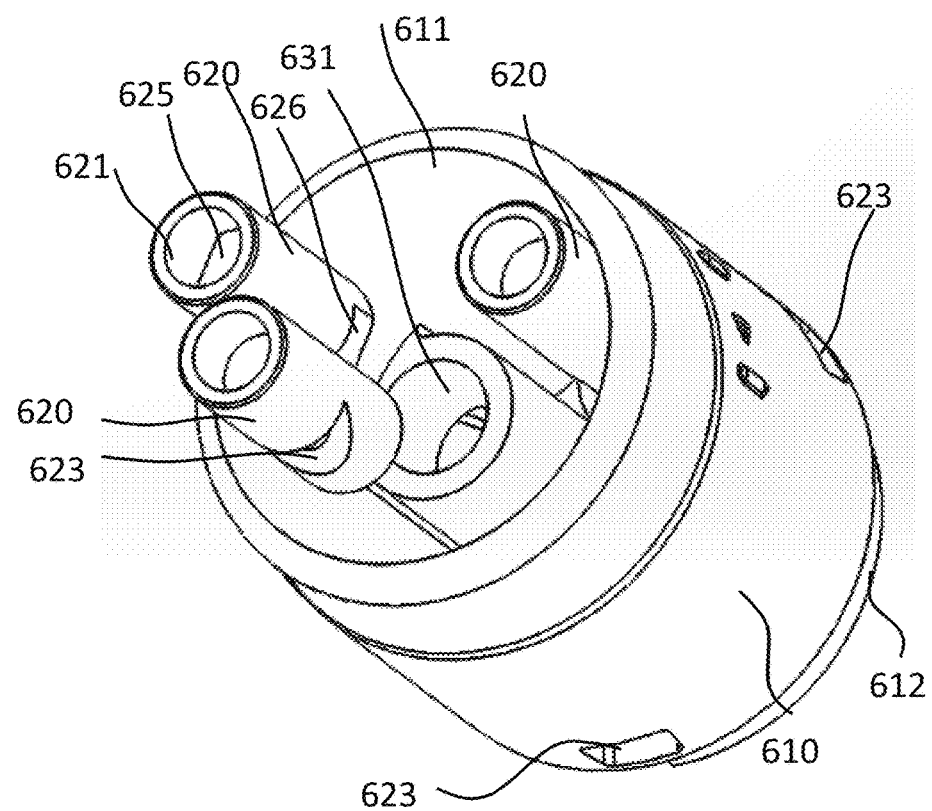
Figure 6C:
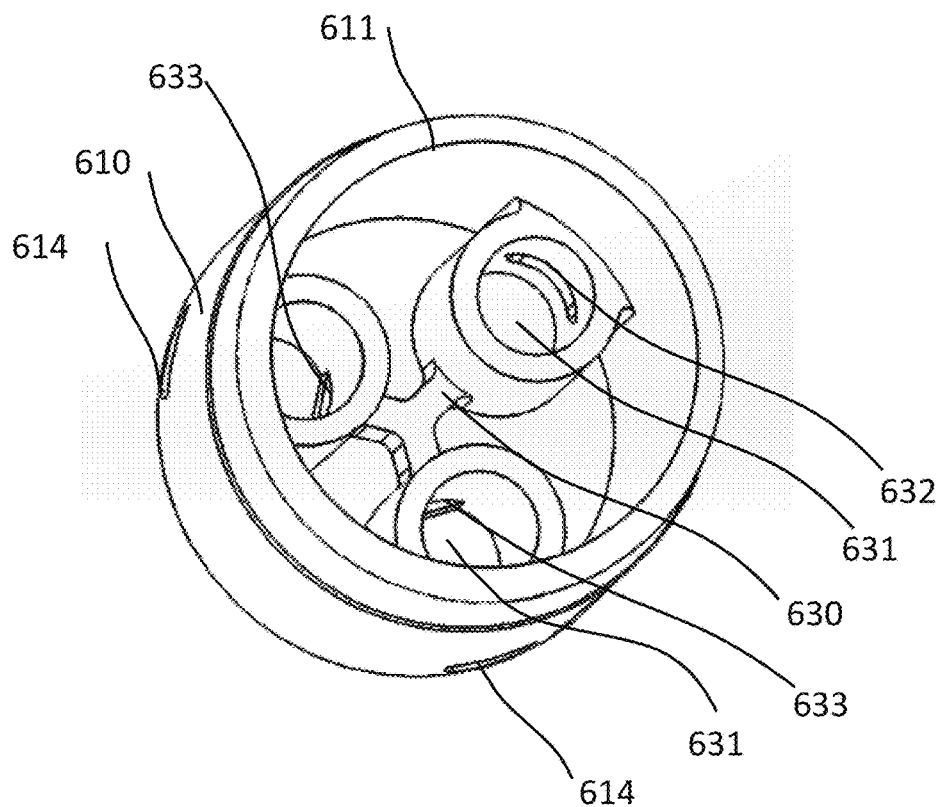
Figure 6D:
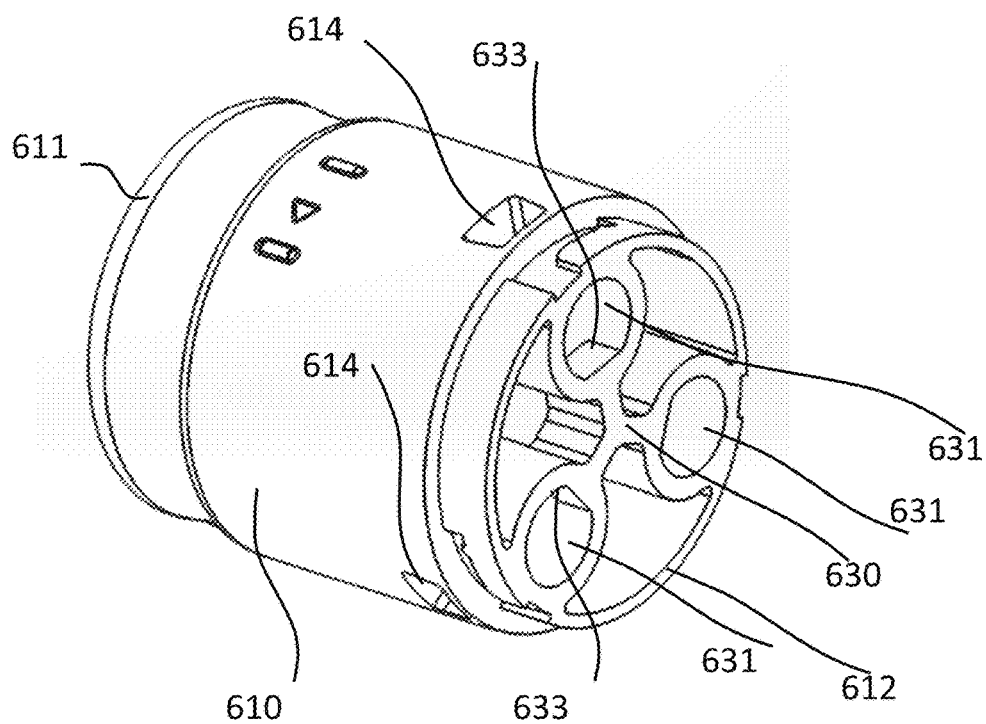

According to the embodiment, by referring to FIG. 6A to FIG. 6C, the application of the proposed mouthpiece tube 600 may be described as below. First, provides a gas flow suction for directing the gas from the entrance end 611 into the space enclosed by the shell 610 of the mouthpiece tube 600. When the gas flow suction begins to function, the gas is directed through the gas entrance 621 of the ultrasonic wave generation device 620. Then, the gas is delivered through the spoiler 625 and the gas exit 623 for generating an ultrasonic wave gas flow, and finally is delivered through the gas opening 614 to the exterior of the space enclosed by the shell 610. In the meantime, by using an ultrasonic wave detection device, the breath function may be distinguished by measuring and calculating the maximum flow rate of the expiration or deciding whether the gas flow rate exceeds the threshold value. Besides, the direction of the gas delivered into the gas entrance 611 is parallel to the direction of the gas delivered into the gas entrance 621 of the ultrasonic wave generation device 620 but is orthogonal to the direction of the gas delivered away the gas opening 614.

Although the invention has been explained in relation to its preferred embodiments, it is to be understood that modifications and variations can be made without departing the spirit and scope of the invention a claimed.

The invention claimed is:

1. A mouthpiece tube, comprising:
a shell, one end of the shell being an exit end and another end of the shell being a shell bottom, the shell bottom comprising at least one channel which has a channel opening and a gas opening, wherein the channel opening is connected to the exterior of the mouthpiece tube, outside a gas flow space enclosed by the shell, wherein the gas opening and the exit end form the gas flow space, and wherein the mouthpiece tube delivers a gas from the gas flow space to the exit end by a gas flow suction; and
at least one ultrasonic wave generation device, wherein different ultrasonic wave generation devices are positioned in different channels, wherein each ultrasonic wave generation device comprises a gas entrance and a gas exit, wherein the gas exit is connected to the gas opening of the channel for delivering the gas from an inner space inside the ultrasonic wave generation device into the gas flow space, wherein the ultrasonic wave generation device delivers the gas from the exterior of the mouthpiece tube through the gas entrance by the gas flow suction, and wherein the inner space is distributed essentially between the gas entrance and the gas exit.

2. The mouthpiece tube of claim 1, wherein the shell bottom includes at least one groove which is positioned between two neighboring channels and faces to the exit end.

3. The mouthpiece tube of claim 1, wherein the shell bottom further includes a gas aperture which is connected to the exterior of the mouthpiece tube for introducing gas into and reducing a gas flow resistance of the gas flow space.

4. The mouthpiece tube of claim 1, wherein the ultrasonic wave generation device further includes a spoiler, wherein the spoiler is positioned inside the ultrasonic wave generation device and placed between the gas entrance and the gas exit so as to form a narrow channel inside the inner space of the ultrasonic wave generation device.

5. The mouthpiece tube of claim 1, wherein the gas exit is positioned in the middle portion of the ultrasonic wave generation device.

6. The mouthpiece tube of claim 1, wherein the gas flow path from the gas entrance into the ultrasonic wave generation device is orthogonal to the gas flow path from the gas exit to the exit end of the shell.

7. The mouthpiece tube of claim 1, wherein the direction that the gas is delivered through the gas entrance into the ultrasonic wave generation device is orthogonal to the direction that the gas is delivered through the gas exist away from the ultrasonic wave generation device.

* * * * *